US00PP11488P

United States Patent [19]

Brown

[11] Patent Number: Plant 11,488

[45] Date of Patent: Aug. 22, 2000

[54] DIASCIA PLANT NAMED 'STRAWBERRY SUNDAE'

[75] Inventor: Graham Noel Brown, Baulkam Hills, Australia

[73] Assignee: The University of Sydney Plant Breeding Institute, Cobbitty, Cobbitty, Australia

[21] Appl. No.: 09/195,600

[22] Filed: Nov. 19, 1998

[51] Int. Cl.[7] ..... A01H 5/00

[52] U.S. Cl. ..... Plt./263

[58] Field of Search ..... Plt./263

*Primary Examiner*—Howard J. Locker
*Assistant Examiner*—Michelle Kizilkaya
*Attorney, Agent, or Firm*—C. A. Whealy

[57] ABSTRACT

A new and distinct cultivar of Diascia plant named 'Strawberry Sundae', characterized by its compact, open and uniform growth habit; freely basally branching plant habit, plants do not require pinching; and numerous bright pink flowers that are about 2 cm in length and 2.4 cm in width.

2 Drawing Sheets

BACKGROUND OF THE INVENTION

The present invention relates to a new and distinct cultivar of Diascia plant, botanically known as *Diascia barberae* hybrid and referred to by the cultivar name 'Strawberry Sundae'.

The new Diascia is a product of a planned breeding program conducted by the Inventor in Cobbitty, New South Wales, Australia. The objective of the program is to create new Diascia cultivars that flower early, are basally branching, have uniform plant habit and attractive flower color.

The new Diascia originated from a cross by the Inventor in 1992 of an unidentified selection of *Diascia barberae* as the female, or seed, parent with the nonpatented *Diascia barberae* cultivar 'Lilac Belle' as the male, or pollen, parent. The cultivar 'Strawberry Sundae' was discovered and selected by the Inventor in 1993 as a flowering plant within the progeny of the stated cross in a controlled environment in Cobbitty, New South Wales, Australia.

Asexual reproduction of the new Diascia by terminal cuttings taken in a controlled environment in Cobbitty, New South Wales, Australia, has shown that the unique features of this new Diascia are stable and are reproduced true to type in successive generations.

SUMMARY OF THE INVENTION

The new Diascia has not been observed under all possible environmental conditions. The phenotype may vary somewhat with variations in environment such as temperature, daylength and light intensity, without, however, any variance in genotype.

The following characteristics have been repeatedly observed and are determined to be basic characteristics of 'Strawberry Sundae' and distinguish 'Strawberry Sundae' as a new and distinct cultivar:

1. Compact, open and uniform growth habit.

2. Freely basally branching plant habit, plants do not require pinching.

3. Numerous bright pink flowers that are about 2 cm in length and 2.4 cm in width.

Compared to plants of the female parent, the unidentified selection of *Diascia barberae*, plants of the new Diascia are more compact, have smaller flowers, and differ in flower color.

Compared to plants of the male parent, the cultivar 'Lilac Belle', plants of the new Diascia are more upright, flower earlier, have larger flowers and differ in flower color.

Plants of the new Diascia can be compared to nonpatented Diascia cultivar 'Ruby Fields'. However, in side-by-side comparisons conducted in Cobbitty, New South Wales, Australia, plants of the new Diascia are more compact and differ in flower color.

Plants of the new Diascia can also be compared to nonpatented Diascia cultivar 'Elliots'. However, in side-by-side comparisons conducted in Cobbitty, New South Wales, Australia, plants of the new Diascia have finer stems, finer leaves and flower earlier.

BRIEF DESCRIPTION OF THE PHOTOGRAPHS

The accompanying colored photographs illustrate the overall appearance of the new Diascia, showing the colors as true as it is reasonably possible to obtain in colored reproductions of this type.

The photograph on the first sheet comprises a top perspective view of a typical potted plant of 'Strawberry Sundae'.

The photograph on the second sheet comprises a closeup view of typical flowering stems of 'Strawberry Sundae'. Flower and foliage colors in the photographs may appear different from the actual colors due to light reflectance.

DETAILED BOTANICAL DESCRIPTION

The following observations, measurements, values, and comparisons describe plants grown in Bonsall, Calif., under outdoor full-sun conditions with day temperatures ranging from 18 to 35° C., night temperatures ranging from 13 to 18° C. Color references are made to The Royal Horticultural Society Colour Chart except where general terms of ordinary dictionary significance are used.

Botanical classification: *Diascia barberae* cultivar 'Strawberry Sundae'.

Parentage:

*Male or pollen parent.*—*Diascia barberae* cultivar 'Lilac Belle', not patented.

*Female or seed parent.*—Unidentified selection of *Diascia barberae.*

Propagation:

*Type.*—By cuttings.

*Time to initiate roots.*—Summer: About 10 days at temperatures of 25° C. Winter: About 15 days at temperatures of 20° C.

*Time to develop roots.*—Summer: About 15 days at temperatures of 25° C. Winter: About 20 days at temperatures of 20° C.

*Rooting habit.*—Fine and freely branching.

Plant description:

*General appearance.*—Upright and slightly spreading; open, airy and mounding; herbaceous plant with long thread-like peduncles that hold bright pink zygomorphic flowers above and beyond the foliage. May be annual or perennial depending on temperatures. Suitable for 12.5 to 25-cm containers and hanging baskets. To produce a 12.5-cm finished flowering plant from rooted cuttings, about 8 to 12 weeks are required depending on temperature and light level.

*Plant height.*—About 30 cm from soil level to top of flowers.

*Plant diameter or spread.*—About 45 cm.

*Branching.*—Freely basally branching, pinching is usually not required.

*Growth rate/vigor.*—Moderately vigorous.

*Stem description.*—Appearance: Thin upright stems give an airy appearance to plant. Quantity of lateral branches: Typically about 150 per plant. Lateral branch length: About 30 cm. Lateral branch diameter: About 1.5 mm. Internode length: Vegetative growth: About 1 to 2 cm. Reproductive growth: About 5 cm. Texture: Glabrous. Color: 146A.

*Foliage description.*—Arrangement: Opposite. Quantity: About 17 per lateral branch. Shape: Deltoid/ovate; apex, acute; base, rounded truncate. Length: Typically about 2.1 cm. Width: About 1.2 cm. Margin: Serrate. Texture: Smooth. Petiole length: About 3 mm. Petiole diameter: About 2 mm. Color: Young leaves, upper surface: 146A. Young leaves, lower surface: 147C. Fully expanded leaves, upper surface: 147A. Fully expanded leaves, lower surface: 147C. Petiole: 147B.

Flowering description:

*Flowers.*—Solitary flowers arranged on terminal racemes; five-lobed, zygomorphic with double nectar spur; flowers develop when peduncles are about 9 cm in length. Flowers held above foliage on long threadlike peduncles. Flowers maintain good color and substance for about 1 week. Flowers self-cleaning.

*Natural flowering season.*—Natural flowering season is spring to fall; flowering continuous during this period.

*Quantity of flowers.*—Very floriferous with typically about 17 open flowers and flower buds per raceme; more than 500 open flowers and flower buds per plant.

*Flower width.*—About 2.4 cm.

*Flower length.*—About 2 cm.

*Flower depth.*—About 1.2 cm.

*Flower aspect.*—Tipped upward and outward.

*Rate of flower opening.*—About 5 days depending on temperature.

*Fragrance.*—None detected.

*Flower buds.*—Shape: Oval. Length: About 5 mm. Diameter: About 5 mm. Color: 73B to 73C.

*Petals.*—Arrangement: Two upper banner petals, two lateral petals and one larger basal lip petal; fused. Base of two banner petals form a small yellow indentation just above the reproductive organs. Center of two lateral petals form curved nectar spurs with darker pink spots at top of spur. Rounded lip petal is much larger and forms a nearly horizontal "platform". Shape: Rounded. Margin: Entire. Length: Banner petals: About 7 mm. Lateral petals: About 1.2 cm. Lip petal: About 1.2 cm. Width: Banner petals: About 1 cm. Lateral petals: About 7 mm. Lip petal: About 1.4 cm. Spur length: About 1 cm. Texture: Smooth, velvety. Color: When opening, upper surface: 73A. When opening, lower surface: 73C. Mature, upper surface: 73A to 73B with yellow eye, 4A, at base of banner and dark fuchsia at base, 58A, surrounding style; color resists fading. Mature, lower surface: 73C. Nectar spurs: 61B to 61C.

*Sepals.*—Quantity: Five-parted, star-shaped calyx. Shape: Elliptic; apex, acute. Margin: Entire. Calyx length: About 4 mm. Calyx width: About 5 mm. Texture: Smooth. Color: Upper surface: 144B. Lower surface: 144A.

*Pedicel.*—Length: About 1.2 cm. Strength: Weak, thread-like. Angle: Acute. Texture: Smooth. Color: 146B.

*Androecium.*—Stamen number: Three per flower. Anther shape: Two-lobed. Anther size: Less than 1 mm. Anther color: 7A. Amount of pollen: Scarce. Pollen color: 7A.

*Gynoecium.*—Pistil number: One per flower. Stigma shape: Rounded. Pistil length: About 2 mm. Style color: 144B. Stigma color: 157B. Ovary color: 144A.

Disease resistance: Disease resistance to pathogens common to Diascia has not been documented.

Seed production: Seed production has not been observed.

It is claimed.

1. A new and distinct cultivar of Diascia plant named 'Strawberry Sundae', as illustrated and described.

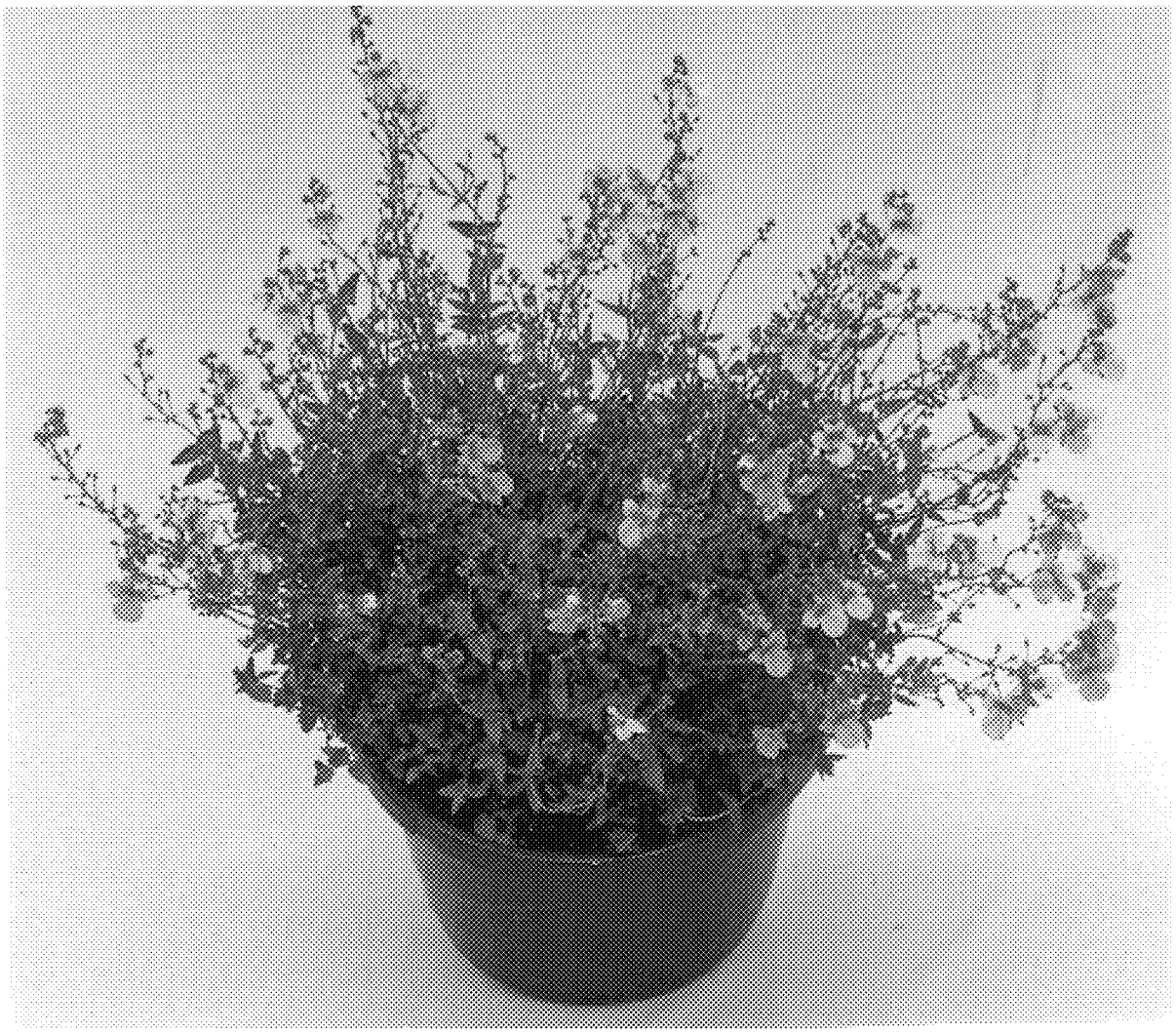

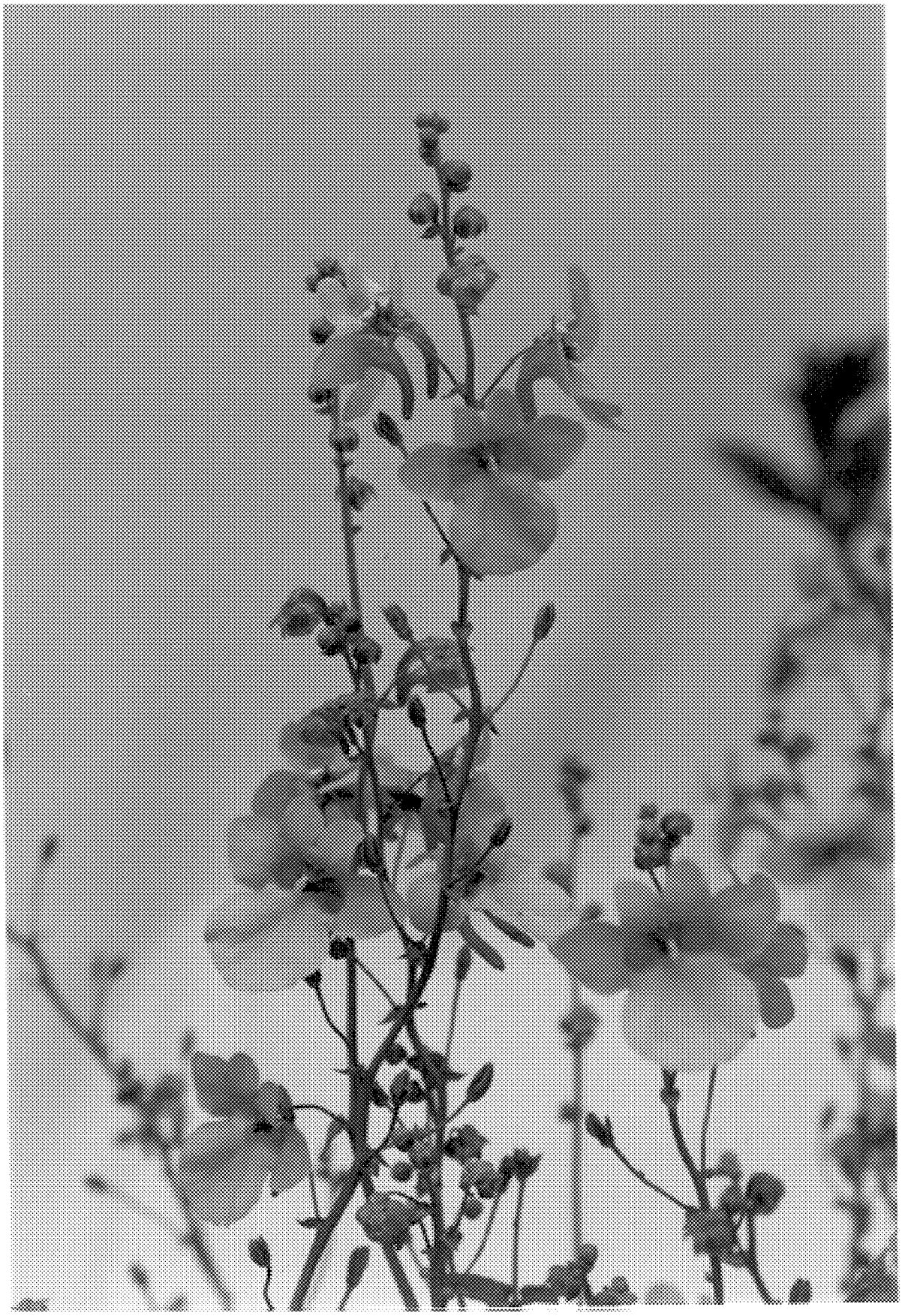

* * * * *